United States Patent [19]

Rasmussen

[11] 4,101,659

[45] Jul. 18, 1978

[54] BENZHYDRYL GUANIDINES

[75] Inventor: Chris Royce Rasmussen, Ambler, Pa.

[73] Assignee: McNeil Laboratories, Incorporated, Fort Washington, Pa.

[21] Appl. No.: 828,694

[22] Filed: Aug. 29, 1977

[51] Int. Cl.$^2$ ............... C07D 295/12; A61K 31/535
[52] U.S. Cl. ............... 424/248.56; 424/246; 424/250; 424/267; 424/274; 424/326; 260/243.78; 260/326.5 L; 260/326.85; 260/564 A; 260/501.14; 544/59; 544/398; 544/402; 544/394; 544/392
[58] Field of Search ............... 544/162, 59; 260/293.78, 268 PH, 268 BZ, 326.85, 326.5 L; 424/248.56, 246, 250, 267, 274

[56] References Cited

U.S. PATENT DOCUMENTS

| 1,805,889 | 5/1931 | Schoeller et al. | 260/326.86 |
|---|---|---|---|
| 3,274,230 | 9/1966 | Braun | 260/293.78 |

*Primary Examiner*—Henry R. Jiles
*Assistant Examiner*—R. W. Ramsuer
*Attorney, Agent, or Firm*—Salvatore R. Conte

[57] ABSTRACT

Benzhydryl derivatives of guanidine (Formula I) having blood sugar lowering activity; pharmaceutical hypoglycemic compositions thereof and methods of administering same to hyperglycemic individuals.

23 Claims, No Drawings

BENZHYDRYL GUANIDINES

BACKGROUND OF THE INVENTION

It has been discovered that the benzhydryl derivatives of Formula (I) are useful in the treatment of hyperglycemic situations in mammals. The compounds are formulated with pharmaceutical carriers for oral and parenteral means of administration for blood sugar lowering uses. In addition to their hypoglycemic activity disclosed herein, certain of the benzhydryl derivatives of Formula (I) have been disclosed in my co-pending U.S. patent application Ser. No. 752,588 as precursors for making heterocyclic derivatives of quanidine as described therein.

In U.S. Pat. No. 3,961,056, certain benzyl derivatives of guanidine are described as having anti-arrhythmic and diuretic uses. However, no benzhydryl derivatives of guanidine are described.

DESCRIPTION OF THE PREFERRED EMBODIMENTS

This invention relates to benzhydryl derivatives of guanidine having hypoglycemic activity and, more particularly, to such derivatives having the formula:

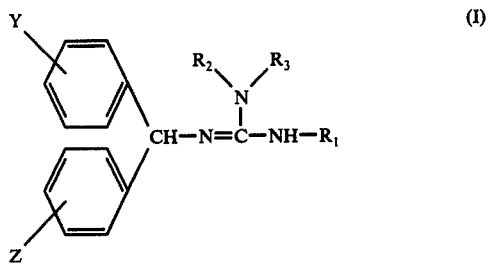

wherein:
$R_1$ is a member selected from the group consisting of hydrogen and loweralkyl, preferably methyl and ethyl;

$R_2$ is a member selected from the group consisting of hydrogen and loweralkyl, preferably methyl and ethyl;

$R_3$ is a member selected from the group consisting of hydrogen, loweralkyl, preferably methyl and ethyl, and cycloalkyl, preferably cyclopentyl and cyclohexyl;

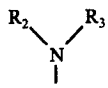

taken together may represent a member selected from the group consisting of

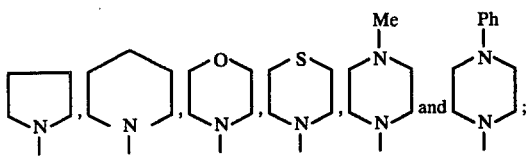

and
Y and Z are each a member selected from the group consisting of hydrogen, halo, loweralkyl, preferably methyl, and loweralkyloxy, preferably methoxy and ethoxy.

The novel benzhydryl guanidine compounds of Formula (I) as free bases are generally soluble in many common polar and non-polar organic solvents such as aromatic hydrocarbons, e.g., benzene, toluene, and the like; haloaromatic hydrocarbons, e.g., chlorobenzene, 1,2-dichlorobenzene, and the like; haloaliphatic hydrocarbons, e.g., chloroform, methylene dichloride, 1,2-dichlorethane and the like; lower alkanols, e.g., methanol, isopropanol, t-butanol and the like, ethers, e.g., diethyl ether, dioxane and the like, and ketones, e.g., acetone, 2-butanone and the like. They are preferably obtained and employed in the form of their acid addition salts which are generally white crystalline solids soluble in water and polar solvents such as the lower alkanols, ketones and the like.

The non-toxic, therapeutically acceptable acid addition salts of the Formula (I) compounds are also embraced within the scope of this invention. Suitable acids may be inorganic acids such as hydrochloric, hydrobromic, hydroiodic, phosphoric, nitric and the like acids, or organic acids such as acetic, propionic, glycolic, pamoic, pyruvic, malonic, succinic, maleic, fumaric, malic, tartaric, citric, benzoic, cinnamic, mandelic, methanesulfonic, ethanesulfonic, benzenesulfonic, p-toluenesulfonic, cyclohexanesulfamic, salicylic, p-aminosalicylic and the like acids. The preferred acid addition salts are the hydrohalic addition salts.

As used herein, the term "loweralkyl" refers to a straight or branch chained hydrocarbon radical having from 1 to 5 carbons, such as, for example, methyl, ethyl, propyl, isopropyl, n-butyl, t-butyl, pentyl, isoamyl and the like; and the term "halo" represents a halogen of atomic weight less than 127, i.e., chloro, bromo, fluoro and iodo.

The compounds of Formula (I) are conveniently prepared by reacting a methylthio compound of Formula (II), wherein $R_1$, Y and Z are as previously defined, in acid addition salt (HX) form with an appropriate amine of Formula (III), wherein $R_2$, $R_3$ and $-NR_2R_3$ are as previously defined, preferably utilizing a stoichiometric excess of (III), in a loweralkanol solvent such as isopropanol and t-butanol and generally at reflux temperatures to yield the benzhydryl guanidine compounds of Formula (I) in acid addition salt form which are readily transformed into the corresponding base form by conventional treatment with suitable alkali. Alternatively, the reaction of (II) with (III) may be performed utilizing approximately equimolar amounts in which case up to an equimolar amount of a suitable tertiary amine, such as, for example, triethylamine, tripropylamine and the like, is preferably added in order to enhance the rate of reaction. The foregoing reaction may be illustrated as follows:

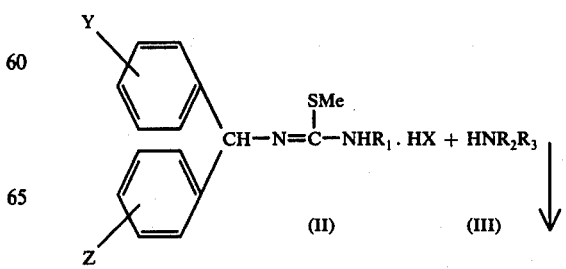

-continued

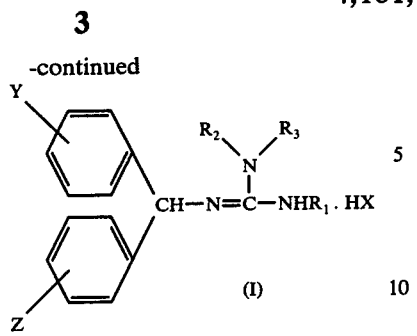

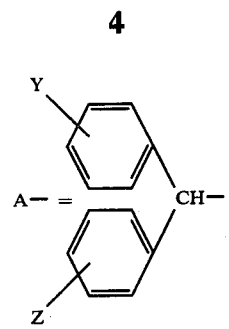

The precursors of Formula (II) are obtainable by methodologies reported in the literature. For example, the compound wherein Y, Z and $R_1$ all equal hydrogen may be prepared according to S. O. Winthrop et al., J. Am. Chem. Soc., 79, 3496 (1957), which describes the reaction of benzhydryl amine, preferably as the hydrochloride salt, with ammonium thiocyanate to yield N-benzhydryl thiourea which is then methylated by standard S-methylation techniques to yield methyl N-benzhydrylcarbamimidothioate as an acid addition salt.

Alternatively, the precursors of Formula (II) may be prepared by the following synthetic sequence. The benzhydrylamines of Formula (IV), which compounds and methods of preparing same are known in the literature, are transformed into the corresponding benzhydryl isothiocyanates of Formula (V) according to the method described by J. C. Jochims et al, Angew. Chem. Internat. Ed., 6 (2), 174 (1967), which method involves the interaction of (IV) with excess carbon disulfide in the presence of an equimolar amount of dicyclohexylcarbodiimide (DCC) at initial temperatures preferably below 0° C in anhydrous ether.

The resultant benzhydryl isothiocyanate (V), which may be isolated from the reaction mixture and purified by conventional means, is then converted to the corresponding N-benzhydrylthiourea of Formula (VI) by the reactions of (V) with ammonia or a primary amine of the formula, $R_1NH_2$, wherein $R_1$ is a substituent as previously defined, preferably in an ethereal solvent such as, for example, diethyl ether, tetrahydrofuran (THF), dioxane, 1,2-dimethoxyethane and the like at about 0° C to ambient temperature.

The thus-obtained N-benzhydrylthiourea (VI), which may be isolated from the reaction mixture and purified by conventional techniques, is then subjected to S-methylation according to methodologies reported in the literature for the conversion of thioureae to S-methylpseudothioureas, e.g., see Winthrop et al., loc. cit., which utilize methyl iodide and methyl chloride as the methylating agent. Other methylating agents which may be employed include methyl mesylate, methyl tosylate, methyl fluorosulfonate and the like. The preferred methylating agent is methyl iodide. In general, the S-methylated product (II) is obtained in the form of an acid addition salt (HX).

The foregoing synthetic sequence may be illustrated by the following flow diagram in which the heretofore-described benzhydryl moiety is represented by the letter "A."

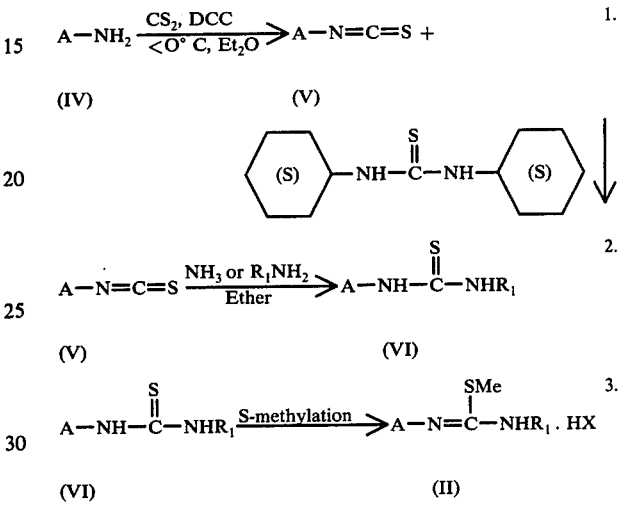

The compounds represented by Formula (I) and the acid addition salts thereof are useful as hypoglycemic agents suitable for lowering blood sugar. This property may be demonstrated by the rat glucose tolerance test, an extremely sensitive standard procedure used in the diagnosis of diabetes and hypoglycemic disease states.

In this test, male Sprague-Dawley rats (Charles River 184–250 grams) are given water ad libitum and fasted 24 hours prior to the experiment. Two to five rats are used for each test and control group. Test compounds, 0.5–100 mg./kg., are administered (s.c., i.p. or orally) suspended in 0.5 or 1.0 milliliter, but preferably the former, of 0.5–1.0% methylcellulose vehicle. Control animals are given an equal amount of vehicle. Serial blood samples (0.1 milliliter) are obtained from the tail without anesthesia prior to and at 30, 60, 90, 120, 150 and 180 minutes after administration of 0.8 to 1.0 gram of glucose per kilogram of body weight in 1 milliliter of water. (The glucose is given orally if the test compound has been given parenterally, and subcutaneously if the test compound has been given orally.) Specimens of blood are immediately deproteinized with aqueous solutions of $Ba(OH)_2$ and $ZnSO_4$ and glucose levels are determined using the glucose oxidase assay described by L. P. Cawley et al., "Ultra Micro Chemical Analysis of Blood Glucose with Glucose Oxidase," Amer. J. Clin. Path., 32, 195 (1959). The blood glucose values at each time point are expressed in terms of milligram percent (mg. glucose/100 ml. of blood). The mean glucose values of the controls are compared statistically by the Student's t-Test to the means of the experimental group at each of the corresponding time points. If the compound lowers the blood glucose significantly at any time at a 95% confidence limit, the compound is considered to have hypoglycemic activity. The blood glucose lowering, expressed as percent lowering, is obtained by dividing the difference between the mean blood glucose values for test and control animals by the mean glucose value for the control animal.

For reducing blood glucose, the compounds of Formula (I) may be employed at a dosage range of about 0.5-100 mg./kg. body weight. It has been found, for example, that administration of the most preferred compounds, the acid addition salts of N-benzhydryl-1-pyrrolidinecarboximidamide or N-benzhydryl-4-morpholine-carboximidamide, at 1-10 mg./kg. body weight p.o. provides a marked lowering of blood sugar in test animals.

In view of the aforementioned hypoglycemic activity of the Formula (I) compounds and salts thereof, this invention provides valuable methods and compositions comprising the said compounds as the active hypoglycemic ingredient in a pharmaceutically acceptable solvent or carrier and, in addition, it provides an effective method of lowering blood glucose levels, for example, in diabetic conditions.

To prepare the pharmaceutical compositions of this invention, a benzhydryl guanidine of Formula (I) or acid addition salt thereof, as the active hypoglycemic ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g, tablet, capsule, powder, injection, teaspoonful and the like, from about 10 to about 500 mg. of the active ingredient, and, preferably, from about 10 to about 250 mg.

The foregoing compositions are particularly suitable for use in lowering blood glucose levels by a method comprising internally administering to a hyperglycemic mammal compositions comprising an effective hypoglycemic amount of a benzhydryl guanidine of Formula (I), preferably as an acid addition salt.

Typical benzhydryl guanidine derivatives of Formula (I) which may be prepared according to the synthetic procedures described herein by using appropriate precursors are:

N-(4,4'-dichlorobenzhydryl)-4-thiamorpholinecarboximidamide;

N-(4,4'-dichlorobenzhydryl)-N',N'-diethylguanidine;
N-(4-chlorobenzhydryl)-N'-cyclohexyl-N'-methylguanidine;
N-(4-chlorobenzhydryl)-N'-ethyl-N',N'''-dimethylguanidine;
N-(4,4'-diethoxybenzhydryl)-N'-ethyl-1-piperidinecarboximidamide;
N-(4,4'-diethoxybenzhydryl)-N'-ethyl-1-pyrrolidinecarboximidamide;
N-(4,4'-dimethoxybenzhydryl)-N'-cyclopentyl-N'-methylguanidine;
N-(4,4'-dimethoxybenzhydryl)-4-morpholinecarboximidamide;
N-(4,4'-dimethoxybenzhydryl)-1-(4-phenylpiperazine)carboximidamide;
N-(4,4'-dibromobenzhydryl)-1-piperidinecarboximidamide;
N-(3-bromobenzhydryl)-4-thiamorpholinecarboximidamide;
N-(3-bromobenzhydryl)-N'-methyl-4-thiamorpholinecarboximidamide;
N-(4-chlorobenzhydryl)-1-(4-methylpiperazine)carboximidamide;
N-(4-chlorobenzhydryl)-N'-cyclohexyl-N'-methylguanidine;
N-(4,4'-diethoxybenzhydryl)-N',N'-diethylguanidine;
N-(4,4'-diethoxybenzhydryl)-1-pyrrolidinecarboximidamide;
N-(4,4'-dimethylbenzhydryl)-4-morpholinecarboximidamide;
N-(4,4'-dimethylbenzhydryl)-N',N'-diethylguanidine;
N-(4-methylbenzhydryl)-N'-cyclohexyl-N'-methylguanidine;
N-(4-methylbenzhydryl)-N'-ethyl-N'-methylguanidine;
N-(4-methoxybenzhydryl)-N'-cyclopentyl-N'-methylguanidine;
N-(4-methoxybenzhydryl)-1-pyrrolidinecarboximidamide; and
N-(4-methoxybenzhydryl)-4-morpholinecarboximidamide.

In view of their structure, the compounds of Formula (I) are inherently capable of existing in tautometric forms (I-a) and (I-b):

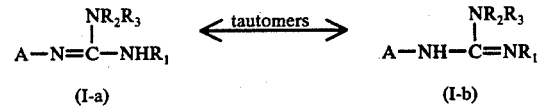

Furthermore, when the benzhydryl substituents Y and Z are non-identical or in different positions on their respective phenyl rings, it is evident that optical isomeric forms (d- and l-) of the Formula (I) products are possible. For example, by utilizing an appropriate resolved (d- or l-) benzhydrylamine of Formula (IV) as a precursor in the synthetic sequence previously described, the final Formula (I) product thus-obtained will similarly be a d- or l-optical isomer.

In the following examples, the term "benzhydryl" and "diphenylmethyl" are equivalent. Furthermore, the terms "guanidine" and "N-carboxidamide" are utilized as dictated for purposes of clarity according to the structure of the particular compound of Formula (I) under consideration.

Following are specific examples of compounds of Formula (I) which can be compounded into pharmaceutical compositions and used within the scope of this invention. These examples are not intended to be limitations upon the broad scope of the invention but merely illustrative.

EXAMPLE I

A. N-Diphenylmethyl-1-pyrrolidinecarboximidamide Hydroiodide

To 76.88g (0.2 mole) of methyl-N-(diphenylmethyl)-carbamimidothioate hydroiodide in t-BuOH (120 ml) is added 28.44g (0.4 mole) of pyrrolidine. The resulting mixture is allowed to heat under reflux on the steam bath for 3½ hours. The reaction mixture is cooled to room temperature affording crystals of crude HI salt, mp. 200°–203° C. Recrystallization from tert-BuOH gives pure N-diphenylmethyl-1-pyrrolidinecarboximidamide hydroiodide; mp. 205°–206° C.

B. N-Diphenylmethyl-1-pyrrolidinecarboximidamide Hydrochloride Hemihydrate

Conversion of the HI salt of Example IA to the free base in $CH_2Cl_2$ by treatment with cold 20% NaOH; drying the organic layer over $K_2CO_3$, filtration, and solvent removal in vacuo gives the free base. Treatment of the free base in moist isopropanol with HCl gas furnishes the crude hydrochloride hemihydrate. The crystals are recrystallized from i-PrOH to give the pure salt; N-diphenylmethyl-1-pyrrolidinecarboximidamide hydrochloride hemihydrate; m.p. 230°–233° C.

EXAMPLE II

N-(Diphenylmethyl)-4-morpholinecarboximidamide 1-(Diphenylmethyl)-2-methyl-2-thiopseudourea hydriodide (19.2g., 0.05 mole) in 75 ml. tert-butanol is heated at reflux for 24 hours with morpholine (8.7 g., 0.1 mole) under a slow stream of nitrogen. The effluent gas is passed through sodium hypochlorite and sodium hydroxide traps to remove the methyl mercaptan formed in the reaction. The mixture was taken to dryness in vacuo and the residue was treated with 3N sodium hydroxide. Extraction with methylene chloride, washing the combined extracts with water, drying over potassium carbonate, filtration and solvent removal under reduced pressure furnishes an oil which solidifies on standing. Recrystallization several times from acetone-ether gives N-(diphenylmethyl)-4-morpholinecarboximidamide as a white solid; mp 122°–124° C.

EXAMPLE III

N,N-Diethyl-N'-diphenylmethylguanidine Hydroiodide

To a suspension of 9.61g (0.025 mole) of methyl-N-(diphenylmethyl)-carbamimidothioate hydroiodide in 20 mls of t-BuOH is added 3.66g (0.05 mole) of diethylamine. The mixture is heated under reflux for 20 hours (trapping the methyl mercaptan formed in the reaction with NaOH and NaOCl sol'n). About two additional mls of diethyl amine is added and refluxing is resumed for another 4 hours. The resulting white solid is filtered from the cooled reaction mixture and washed with t-BuOH and ether to yield crude product mp 187°–9° C. The pure product, N,N-diethyl-N-diphenylmethylguanidine hydroiodide, is isolated after one recrystallization from 1:1:1 MeOH/i-PrOH/t-BuOH as a white crystalline solid, mp. 187°–189° C.

EXAMPLE IV

N-(Diphenylmethyl)-1-piperidinecarboximidamide Monohydroiodide

To a suspension of 9.61 g (0.025 mole) of methyl-N-(diphenylmethyl)-carbamimidothioate hydroiodide in 20 ml of t-BuOH is added 4.26 g (0.05 mole) of piperidine. The mixture is heated under reflux over night. The resulting crystals after cooling in ice, are filtered; mp 200°–213° C. One recrystallization from methanol-t-BuOH yields the pure product, N-(diphenylmethyl)-1-piperidinecarboximidamide monohydroiodide as a white crystalline solid; mp 207°–210° C.

EXAMPLE V

N-(Diphenylmethyl)-1-(4-methyl)piperazinecarboximidamide Monohydroiodide Hydrate To 8.84 g (0.023 mole) of methyl-N-diphenylmethyl-carbamimidothioate hydroiodide in t-BuOH in added 4.71 g (0.047 mole) of N-methylpiperazine. The resultant mixture is allowed to heat under reflux overnight. The mixture is evaporated to dryness in vacuo then diluted with i-PrOH to give crystals; mp 200°–204° C. The crystals are recrystallized from 2-proponal affording pure product, N-(diphenylmethyl)-1-(4-methyl)piperazinecarboximidamide monohydroiodide hydrate; mp 202°–204° C.

EXAMPLE VI

A. p-Chlorobenzhydryl Isothiocyanate

A mixture of 80 ml of carbon disulfide and 39.82 g (0.193 mole) of dicyclohexylcarbodimide in 100 ml of anhydrous ether, under dry $N_2$, is cooled with stirring to −35° C. Then 42.23 g (0.194 mole) of p-chlorobenzhydrylamine in 500 ml of dry ether is added over about 5 min such that the temperature within the reaction vessel does not rise above −20° C. The temperature is allowed to rise slowly over 3 hrs. to ca.25° C and stirring is continued overnight. Dicyclohexylthiourea was removed by filtration and the filtrate is taken to dryness in vacuo. The cloudy oil is treated with 500 ml of pentane which dissolves the product and precipitates more insoluble impurities. Filtration through filter aid (diatomaceous earth) and solvent removal in vacuo gives p-chlorobenzhydryl isothiocyanate as an oil; IR (neat) 2140 $cm^{-1}$.

B. N-(4-Chlorobenzhydryl)thiourea

A solution of 4-chlorobenzhydryl isothiocyanate [5.2g (0.02M)] in 50 mls of dry ether at 0° C is treated with $NH_3$ (anhyd.) for ½ hour while maintaining a temperature of 0° C with stirring. Stirring is continued an additional 1.5 hours at 9° to 10° C. during which time a white solid appears. The crude thiourea is filtered and washed thoroughly with ether; mp 173°–5° C. The filtrate is concentrated in vacuo to yield additional product. The combined crops of N-(4-chlorobenzhydryl)thiourea are used in the next step without further purification.

C. Methyl N-(4-chlorobenzhydryl)carbamimidothioate Hydroiodide

A solution of 5.3 g (0.019 mole) of N-(4-chlorobenzhydryl)thiourea in 25 ml of methanol is treated with 2.64 g (0.019 mole) of methyl iodide and allowed to stir at room temperature overnight. The methanol is removed in vacuo to yield the crude pseudothiourea as an oil. The oily methyl N-(4-chlorobenzhydryl)carbamimidothioate hydroiodide is used in the next step without further purification.

D.
N-(4-Chlorobenzhydryl)-1-pyrrolidinecarboximidamide Hydroiodide

A mixture of 7.0 g (0.017 mole) of methyl N-(4-chlorobenzhydryl)carbamimidothioate hydroiodide and 2.85 g (0.04 mole) of pyrrolidine in 20 mls of t-BuOH is heated at reflux overnight. The t-BuOH is removed in vacuo and the crude guanidine hydroiodide is crystallized from methanol-ether. The crude product is recrystallized from methanol-t-butanol to yield pure N-(4-chlorobenzhydryl)-1-pyrrolidinecarboximidamide hydroiodide; mp 218°–220° (dec).

EXAMPLE VII

N-Cyclopentyl-N-methyl-N'-(diphenylmethyl)guanidine

To a suspension of 9.1 g (0.025 mole) of methyl N-(diphenylmethyl) carbamimidothioate hydroiodide in 20 mls of t-BuOH is added 3.5 g (0.035 mole) of N-methylcyclopentylamine and 4 mls of triethylamine. The mixture is then heated under reflux overnight. Upon cooling, the crude guanidine hydroiodide forms as an oil that does not crystallize under various conditions. The free base is liberated with 10% NaOH and extracted with $CH_2Cl_2$. The methylene chloride sol'n is dried ($K_2CO_3$) and concentrated to dryness in vacuo to yield 8.0 g of an oil. The free base crystallizes from ether to give N-cyclopentyl-N-methyl-N'-(diphenylmethyl)-guanidine; mp 102°–104° C.

EXAMPLE VIII

N-Diphenylmethyl-4-phenyl-1-piperazinecarboximidamide Monohydroiodide Hemihydrate A mixture of 6.38 g (0.017 mole) of N-benzhydryl-S-methylpseudothiourea monohydroiodide and 5.81 g (0.034 mole) of N-phenylpiperazine in t-BuOH is heated under reflux overnight. About 50 ml of moist 2-propanol is added and the mixture is then allowed to crystallize. The crude guanidine melts at 119°–120° C. Recrystallization from 1:2 MeOH/t-BuOH and then from 2-propanol gives pure N-diphenylmethyl-4-phenyl-1-piperazine-carboximidamide monohydroiodide hemihydrate; mp (113°–117°) 208°–210° C.

EXAMPLE IX

A. N-Benzhydryl-N'-methylthiourea

A solution of 13.50 g (0.06 Mole) of benzhydrylisothiocyanate in ether is saturated with anhydrous methylamine in an ice bath. The crystals are filtered to yield the product, N-benzhydryl-N'-methylthiourea; mp 152°–154° C, which is sufficiently pure for the next step.

B. Methyl N-Diphenylmethyl-N'-methylcarbamimidothioate Hydroiodide

A suspension of 14.64 g (0.057 mole) of N-benzyl-N'-methylthiourea in methanol is treated with 8.09 g (0.057 mole) of methyl iodide and allowed to stir overnight. The solvent is removed in vacuo and the residue dissolved in t-BuOH and 2-propanol. Cooling and scratching yields methyl-N-diphenylmethyl-N'-methylcarbamimidothioate hydroiodide; mp 170°–173° C.

C.
N-(Diphenylmethyl)-N'-methyl-1-pyrrolidinecarboximidamide Hydroiodide Hydrate A mixture of 20.81 g (0.052 mole) of the compound of Example IX B and 7.4 g (0.104 mole) of pyrrolidine in t—BuOH is heated at reflux overnight. Crystals started forming after about two hours of heating. The mixture is filtered to yield crude guanidine; mp 200°–205° C. Recrystallization from t-BuOH yields N-(diphenylmethyl)-N'-methyl-1-pyrrolidinecarboximidamide hydroiodide hydrate; mp 211.5°–213.5° C.

EXAMPLE X

A. 4-Methylbenzhydrylisothiocyanate

A solution of 20.42 g (0.099 mole) of N,N-dicyclohexylcarbodiimide and 40 mls of carbon disulfide in 50 mls of dry $Et_2O$ at $-40°$ C under $N_2$ is treated dropwise with stirring over a 5 min. period (so that temperature does not exceed $-30°$ C) with a solution of 19.7 g (0.1 mole) of 4-methylbenzhydrylamine. The temperature is allowed to rise slowly over 3 hours to ca. 25° C and stirring is continued overnight. The insoluble dicyclohexylthiourea formed is filtered off and the filtrate concentrated in vacuo to an oil. A second crop of the thiourea is obtained via trituration of the crude isothiocyanate with hexane. 4-methylbenzhydrylisothiocyanate is obtained as an oil; IR (net) 2080 cm$^{-1}$. The material is of sufficient purity to use in the next step.

B. N-(4-Methylbenzhydryl)thiourea

A solution of 22 g (0.092 mole) of 4-methylbenzhydrylisothiocyanate in 250 ml of dry ether at 0° is treated with anhydrous $NH_3$ for 3 hours while stirring. The mixture is stirred an additional 1.5 hours at 0° to 10° C during which time the crude product precipitates as a white solid. Filtration and washing with $Et_2O$ affords the product; mp 167°–8° C.

C. Methyl N-(4-Methylbenzhydryl)carbamimidothioate Hydroiodide (and free base)

A suspension of 16.5 g (0.064 mole) of N-(4-methylbenzhydrylthiourea in 75 mls of MeOH is treated with 9.08 g (0.064 mole) of methyl iodide and allowed to stir over night at room temperature. The reaction mixture is concentrated in vacuo to yield 26.5 g (100%) of the crude product, which crystallizes. Recrystallization from t-BuOH affords pure methyl N-(4-methylbenzhydryl) carbamimidothioate hydroiodide; mp 145°–147° C.

The free base of the product is obtained by treatment of the salt with ammonium hydroxide. Recrystallization of the free base from ether-hexane furnishes pure methyl N-(4-methylbenzhydryl)carbamimidothioate; mp 130°–132° C.

D.
N-(4-Methylbenzhydryl)-1-pyrrolidinecarboximidamide Hydroiodide

A mixture of 13.3 g (0.0334 mole) of methyl N-(4-methylbenzhydryl)carbamimidothioate hydroiodide and 5.0 g (0.07 mole) of pyrrolidine in 40 mls of t-BuOH is heated under reflux for 24 hrs. The crude product crystallizes out of the reaction mixture while refluxing. The mixture is allowed to cool over night at room temperature and filtered to yield crude product; mp 227°–30° C. Recrystallization from MeOH/t-BuOH yields the pure N-(4-methylbenzhydryl)-1-pyrrolidinecarboximidamide hydroiodide; mp 229°–230° C, as a white solid.

EXAMPLE XI

By repeating the amine-to-isothiocyanate procedure of Example VI-A or X-A, except that an equivalent amount of an appropriate benzhydrylamine is employed, the following benzhydrylisothiocyanates of Formula (V) are:

4,4'-dichlorobenzhydrylisothiocyanate;
4,4'-diethoxybenzhydrylisothiocyanate;
4-methoxybenzhydrylisothiocyanate;
4,4'-dimethoxybenzhydrylisothiocyanate;
4,4'-dibromobenzhydrylisothiocyanate;
3-bromobenzhydrylisothiocyanate; and
4,4'-dimethylbenzhydrylisothiocyanate.

EXAMPLE XII

The isothiocyanate-to-thiourea procedures of the applicable foregoing examples are followed using appropriate starting materials to yield the following benzhydrylthioureas of Formula (VI):

| Y | Z | $R_1$ |
|---|---|---|
| 4-Cl | 4-Cl | H |
| 4-Cl | H | Me |
| 4-EtO | 4-EtO | Et |
| 4-MeO | 4-MeO | H |
| 4-Br | 4-Br | H |
| 3-Br | H | Me |
| 3-Br | H | H |
| 4-EtO | 4-EtO | H |
| 4-Me | 4-Me | H |
| 4-MeO | H | H |

EXAMPLE XIII

A solution of an appropriate benzhydrylthiourea of Formula (VI) is S-methylated with an appropriate methylating agent (as indicated by the resultant HX salt below) to furnish the following methyl N-benzhydryl-N'-$R_1$-carbamimidothioates of Formula (II) in the form of an acid addition (HX) salt:

| Y | Z | $R_1$ | HX |
|---|---|---|---|
| 4-Cl | 4-Cl | H | methanesulfonate |
| 4-Cl | H | Me | hydroiodide |
| 4-EtO | 4-EtO | Et | p-toluenesulfonate |
| 4-MeO | 4-MeO | H | hydroiodide |
| 4-Br | 4-Br | H | fluorosulfonate |
| 3-Br | H | Me | hydroiodide |
| 3-Br | H | H | hydrochloride |
| 4-EtO | 4-EtO | H | hydroiodide |
| 4-Me | 4-Me | H | hydroiodide |
| 4-MeO | H | H | hydroiodide |

EXAMPLE XIV

By heating an appropriate methyl N-benzhydryl-N'-$R_1$-carbamimidothioate salt of Formula (II) with an appropriate $R_2R_3NH$ amine of Formula (III) in the indicated molar ratios at a reflux temperature in either isopropanol or t-butanol according to the procedures previously described, the following benzhydryl quanidine derivatives of Formula (I) are obtained in the form of the indicated acid addition (HX) salt:

| Y | Z | $R_1$ | $NR_2R_3$ | Moles III/II | Moles $Et_3N$/II | HX |
|---|---|---|---|---|---|---|
| 4-Cl | 4-Cl | H | N(Me)—⟨pyrrolidine⟩ | 2 | — | $HO_3SMe$ |
| 4-Cl | 4-Cl | H | N—⟨pyrrolidine⟩ | 2 | — | $HO_3SMe$ |

-continued

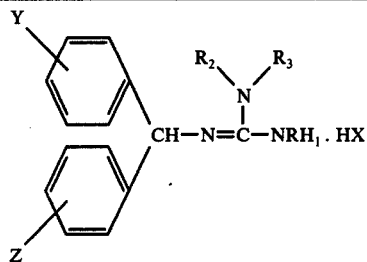

| Y | Z | $R_1$ | $NR_2R_3$ | Moles III/II | Moles $Et_3N/II$ | HX |
|---|---|---|---|---|---|---|
| 4-Cl | H | Me | morpholino (N-O) | 2 | — | HI |
| 4-Cl | H | Me | thiomorpholino (N-S) | 1 | 1 | HI |
| 4-EtO | 4-EtO | Et | morpholino (N-O) | 2 | — | $HO_3S$-4-MePh |
| 4-EtO | 4-EtO | Et | thiomorpholino (N-S) | 1.2 | 1 | $HO_3S$-4-MePh |
| 4-MeO | 4-MeO | H | N-methylpiperazino (N-N—Me) | 2 | — | HI |
| 4-Br | 4-Br | H | pyrrolidino (N) | 2 | — | $HO_3SF$ |
| 3-Br | H | Me | pyrrolidino (N) | 2 | — | HI |
| 3-Br | H | H | N(Me)-cyclopentyl | 1.2 | 1 | HCl |
| 3-Br | H | H | $N(Et)_2$ | 2 | — | HCl |
| 4-Cl | H | H | thiomorpholino (N-S) | 1.2 | 1 | HI |
| 4-EtO | 4-EtO | H | morpholino (N-O) | 2 | — | HI |
| 4-EtO | 4-EtO | H | piperidino (N) | 2 | — | HI |
| 4-Me | 4-Me | H | pyrrolidino (N) | 2 | — | HI |
| 4-Me | 4-Me | H | N(Me)-cyclohexyl | 2 | — | HI |
| 4-Me | H | H | morpholino (N-O) | 2 | — | HI |
| 4-MeO | H | H | N(Me)Et | 2 | — | HI |

What is claimed is:

1. A pharmaceutical composition in dosage unit form comprising an effective hypoglycemic amount of a member selected from the group consisting of a benzhydryl guanidine derivative having the formula:

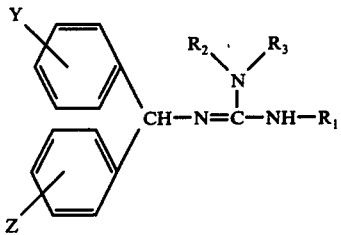

wherein:
R₁ is a member selected from the group consisting of hydrogen and loweralkyl;

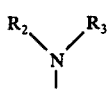

taken together represents a member selected from the group consisting of

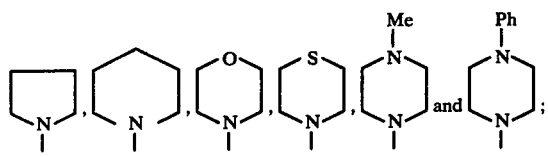

and Y and Z are each a member selected from the group consisting of hydrogen, halo, loweralkyl, and loweralkyloxy;
and the pharmaceutically acceptable acid salts thereof in admixture with a pharmaceutical carrier.

2. A pharmaceutical composition of claim 1 wherein the amount of said benzhydryl guanidine derivative or salt thereof is from about 10 to about 500 mg. per dosage unit.

3. A pharmaceutical composition of claim 1 wherein the amount of said benzhydryl guanidine derivative or salt thereof is from about 10 to about 250 mg. per dosage unit.

4. A pharmaceutical composition of claim 1 wherein the symbol —NR₂R₃ is pyrrolidino.

5. A pharmaceutical composition of claim 1 wherein the symbol —NR₂R₃ is morpholino.

6. A pharmaceutical composition of claim 1 wherein the benzhydryl guanidine derivative is a member selected from the group consisting of N-benzhydryl-1-pyrrolidine-carboximidamide and the pharmaceutically acceptable acid addition salts thereof.

7. A pharmaceutical composition of claim 1 wherein the benzhydryl guanidine derivative is a member selected from the group consisting of N-benzhydryl-4-morpholinecarboximidamide and the pharmaceutically acceptable acid addition salts thereof.

8. A method of lowering blood glucose levels which comprises internally administering to a hyperglycemic mammal a pharmaceutical composition in dosage unit form comprising an effective hypoglycemic amount of a member selected from the group consisting of a benzhydryl guanidine derivative having the formula:

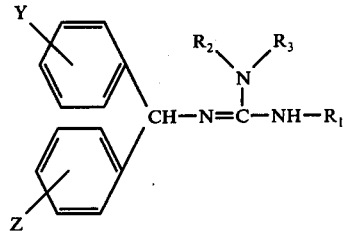

wherein:
R₁ is a member selected from the group consisting of hydrogen and loweralkyl;

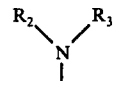

taken together represents a member selected from the group consisting of

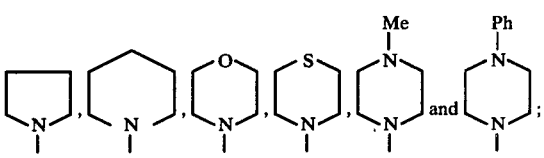

and Y and X are each a member selected from the group consisting of hydrogen, halo, loweralkyl, and loweralkyloxy;
and the pharmaceutically acceptable acid addition salts thereof in admixture with a pharmaceutical carrier.

9. A method according to claim 1 wherein the amount of said benzhydryl guanidine derivative or salt thereof is from about 10 to about 500 mg. per dosage unit.

10. A method according to claim 1 wherein the amount of said benzhydryl guanidine derivative or salt thereof is from about 10 to about 250 mg. per dosage unit.

11. A method according to claim 1 wherein the symbol —NR₂R₃ is pyrrolidino.

12. A method according to claim 1 wherein the symbol —NR₂R₃ is morpholino.

13. A method according to claim 1 wherein the benzhydryl guanidine derivative is a member selected from the group consisting of N-benzhydryl-1-pyrrolidinecarboximidamide and the pharmaceutically acceptable acid addition salts thereof.

14. A method according to claim 1 wherein the benzhydryl guanidine derivative is a member selected from the group consisting of N-benzhydryl-4-morpholinecarboximidamide and the pharmaceutically acceptable acid addition salts thereof.

15. A compound selected from the group consisting of a benzhydryl guanidine derivative having the formula:

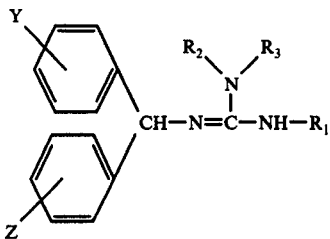

wherein:

R₁ is a member selected from the group consisting of hydrogen and loweralkyl;

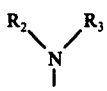

taken together represents a member selected from the group consisting of

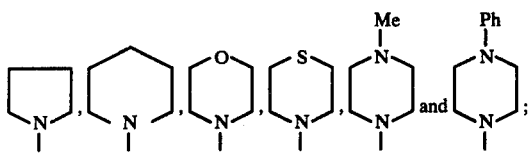

and Y and Z are each a member selected from the group consisting of hydrogen, halo, loweralkyl, and loweralkyloxy;

and the pharmaceutically acceptable acid addition salts thereof.

16. A compound selected from the group consisting of N-benzhydryl-1-pyrrolidinecarboximidamide and the pharmaceutically acceptable acid addition salts thereof.

17. A compound selected from the group consisting of N-benzhydryl-4-morpholinecarboximidamide and the pharmaceutically acceptable acid addition salts thereof.

18. A compound selected from the group consisting of N-benzhydryl-1-piperidinecarboximidamide and the pharmaceutically acceptable acid addition salts thereof.

19. A compound selected from the group consisting of N-benzhydryl-1-(4-methyl)piperazinecarboximidamide and the pharamceutically acceptable acid addition salts thereof.

20. A compound selected from the group consisting of N-(4-chlorobenzhydryl)-1-pyrrolidinecarboximidamide and the pharmaceutically acceptable acid addition salts thereof.

21. A compound selected from the group consisting of N-benzylhydryl-4-phenyl-1-piperazinecarboximidamide and the pharmaceutically acceptable acid addition salts thereof.

22. A compound selected from the group consisting of N-benzhydryl-N'-methyl-1-pyrrolidinecarboximidamide and the pharmaceutically acceptable acid addition salts thereof.

23. A compound selected from the group consisting of N-(4-methylbenzhydryl)-1-pyrrolidinecarboximidamide and the pharmaceutically acceptable acid addition salts thereof.

* * * * *